(12) United States Patent
Zablocki et al.

(10) Patent No.: US 6,440,948 B1
(45) Date of Patent: *Aug. 27, 2002

(54) THIOPHENE $A_{2A}$ RECEPTOR AGONISTS

(75) Inventors: Jeff A. Zablocki, Mountain View; Elfatih O. Elzein, Fremont; Venkata P. Palle, Mountain View, all of CA (US)

(73) Assignee: CV Therapeutics, Inc., Palo Alto, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/597,436

(22) Filed: Jun. 20, 2000

Related U.S. Application Data

(60) Provisional application No. 60/140,478, filed on Jun. 22, 1999.

(51) Int. Cl.[7] .................... A61K 31/70; C07H 19/167
(52) U.S. Cl. ........................ 514/46; 536/27.62
(58) Field of Search ............... 514/46; 536/27.62

(56) References Cited

FOREIGN PATENT DOCUMENTS

| | | | |
|---|---|---|---|
| CA | 965411 | * | 4/1975 |
| CA | 1000696 | * | 11/1976 |
| DE | 2324130 | * | 11/1973 |
| EP | 0 354 638 | | 2/1990 |
| EP | 0508687 | * | 10/1992 |
| JP | 50034039 | * | 11/1975 |

OTHER PUBLICATIONS

Persson et al., "Synthesis and Antiviral Effects of 2–Heteroaryl Substituted Adenosine and 8–Heteroaryl Substituted Guanosine Derivatives," *Bioorganic & Medicinal Chemistry*, 3(10), 1377–1382 (1995); see also *Chemical Abstracts*, 124(9), p. 3120, Abstract No. 117832t (Feb. 26, 1996).*

Marumoto et al. (III), "Synthesis and Coronary Vasodilating Activity of 2–Substituted Adenosines," *Chemical & Pharmaceutical Bulletin* (Japan), 23(4), 759–774 (Apr., 1975).*

Marumoto et al. (IV), "Synthesis and Enzymatic Activity of Adenosine 3', 5'–Cyclic Phosphate Analogs," *Chemical & Pharmaceutical Bulletin* (Japan), 27(4), 990–1003 (Apr., 1979).*

Mager et al., "Molecular Simulation Applied to 2–(N' –Alkylidenehydrazino)–and 2–(N'–Alkylidenehydrazino)adenosine $A_2$ Agonists," *European Journal of Medicinal Chemistry*, 30, 15–25 (1995).*

* cited by examiner

*Primary Examiner*—Johann Richter
*Assistant Examiner*—L Eric Crane
(74) *Attorney, Agent, or Firm*—McDonnell Boehnen Hulbert & Berghoff

(57) ABSTRACT

2-(3-,4-(substituted)-5-alkylthienyl)adenosines and the 5'-uronic acid amide analogues thereof having the following formula:

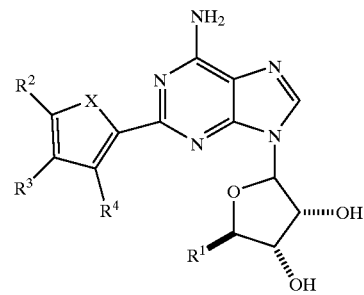

are disclosed herein. Additionally disclosed are medicinal methods of treatment wherein the adenosine $A_{2A}$ agonist activity of the noted compounds stimulates mammalian coronary vasodilation for therapeutic purposes and for purposes of imaging the heart.

16 Claims, No Drawings

THIOPHENE $A_{2A}$ RECEPTOR AGONISTS

This application claims the benefit of provisional application No. 140,478 filed Jan. 22, 1999.

BACKGROUND OF THE INVENTION

1. Field of Invention

This invention includes thiophene compounds that are useful as $A_{2A}$ receptor agonists. The compounds of this invention are vasodialating agents that are useful in heart imaging to aid in the identification of mammals, and especially humans who are suffering from disorders such poor coronary perfusion which is indicative of coronary artery disease (CAD). The compounds of this invention can also be used as therapeutics for coronary artery disease.

2. Description of the Art

Pharmacological stress is frequently induced with adenosine or dipyridamole in patients with suspected CAD before imaging with Tl scintigraphy or echocardiography. Both drugs effect dilation of the coronary resistance vessels by activation of cell surface $A_2$ receptors. Although pharmacological stress was originally introduced as a mean of provoking coronary dilation in patients unable to exercise, several studies have shown that the prognostic value of $^{201}$Tl or echocardiographic imaging in patients subjected to pharmacological stress with adenosine or dipyridamole was equivalent to patients subjected to traditional exercise stress tests. However, there is a high incidence of drug-related adverse side effects during pharmacological stress imaging with these drugs such as headache and nausea, that could be improved with new therapeutic agents.

Adenosine $A_{2B}$ and $A_3$ receptors are involved in a mast cell degranulation and, therefore, asthmatics are not give the non-specific adenosine agonists to induce a pharmacological stress test. Additionally, adenosine stimulation of the $A_1$ receptor in the atrium and A-V mode will diminish the S-H interval which can induce AV block. (N. C. Gupto et al.; *J Am Coll. Cardiol*, (1992) 19: 248–257). Also, stimulation of the adenosine A1 receptor by adenosine may be responsible for the nausea since the $A_1$ receptor is found in the intestinal tract. (J. Nicholls et al.; *Eur. J. Pharm.*(1997) 338(2) 143–150).

Animal data suggests that specific adenosine $A_{2A}$ subtype receptors on coronary resistance vessels mediate the coronary dilatory responses to adenosine, whereas subtype $A_{2B}$ receptor stimulation relaxes peripheral vessels (note: the latter lowers systemic blood pressure). As a result there is a need for pharmaceutical compounds that are $A_{2A}$ receptor agonists that have no pharmacological effect as a result of stimulating the $A_1$ receptor in vivo. Furthermore, there is a need for $A_{2A}$ receptor agonists that have a short half-life, and that are well tolerated by patients undergoing pharmacological coronary stress evaluations.

SUMMARY OF THE INVENTION

In one aspect, this invention includes 2-adenosine thiophene compounds that are useful $A_{2A}$ receptor agonists.

In another aspect, this invention includes pharmaceutical compositions including 2-adenosine thiophene that are well tolerated with few side effects.

Still another aspect of this invention are thiophene compounds that can be easily used in conjunction with radioactive imaging agents to facilitate coronary imaging.

In one embodiment, this invention includes thiophene compounds having the following formula:

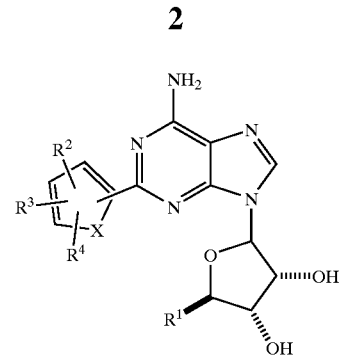

In another embodiment, this invention includes methods for using compounds of this invention to stimulate coronary vasodilatation in mammals, and especially in humans, for stressing the heart induced steal situation for purposes of imaging the heart.

In still another embodiment, this invention is a pharmaceutical composition of matter comprising one or more compounds of this invention and one or more pharmaceutical excipients.

DESCRIPTION OF THE CURRENT EMBODIMENT

The compounds of this invention include a class of thiophene compounds having the following formula:

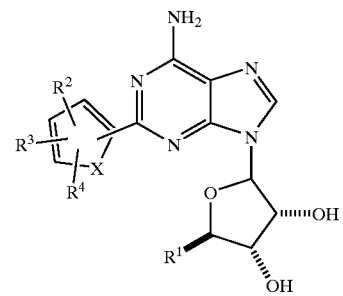

wherein X is S, O and $NR^5$;

$R^1$, is —$CH_2OH$, and —$C(=O)NR^7R^8$;

$R^2$, $R^3$, $R^4$ and $R^5$ are each individually selected from the group consisting of hydrogen, halo, $NO_2$, $CF_3$, CN, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CO_2R^{22}$, $SO_2NR^{20}CON(R^{20})_2$, $N(R^{20})_2NR^{20}COR^{22}$, $NR^{20}CO_2R^{22}$, $NR^{20}CON(R^{20})_2$, $NR^{20}C(NR^{20})NHR^{23}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OC(O)R^{20}$, $C(O)OCH_2OC(O)R^{20}$, $OCON(R^{20})_2$, $C_{1-15}$ alkyl, $C_{2-15}$ alkenyl, $C_{2-15}$ alkynyl, heterocyclyl, aryl, and heteroaryl, which alkyl, alkenyl, alkynyl, $C_{1-15}$ alkoxy, aryl, heterocyclyl, and heteroaryl are optionally substituted with from 1 to 3 substituents independently selected from the group consisting of halo, $NO_2$, heterocyclyl, aryl, heteroaryl, $CF_3$, CN, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CO_2R^{22}$, $SO_2NR^{20}CON(R^{20})_2$, $N(R^{20})_2NR^{20}COR^{22}$, $NR^{20}CO_2R^{22}$, $NR^{20}CON(R^{20})_2$, $NR^{20}C(NR^{20})NHR^{23}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OC(O)R^{20}$, $C(O)OCH_2OC(O)R^{20}$, and $OCON(R^{20})_2$ and wherein each optional heteroaryl, aryl, and heterocyclyl substitution substituent is further optionally substituted with halo, $NO_2$, alkyl, $CF_3$, amino, mono- or di- alkylarnino, alkyl or aryl or heteroaryl amide, $NCOR^{22}$, $NR^{20}SO_2R^{22}$, $COR^{20}$, $C_2R^{20}$, $CON(R^{20})_2$, $NR^{20}CON(R^{20})_2$, $OC(O)R^{20}$, $OC(O)N(R^{20})_2$. $SR^{20}$, $SO_2R^{22}$, $SO_2N(R^{20})_2$, CN, or $OR^{20}$;

$R^7$ and $R^8$ are each independently selected from H, and $C_{1-15}$, alkyl optionally substituted with from 1 to 2 substituents independently selected from the group consisting of halo, $N_2$, heterocyclyl, aryl, heteroaryl, $CF_3$, CN, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CO_2R^{22}$, $SO_2NR^{20}CON(R^{20})_2$, $N(R^{20})_2$ $NR^{20}COR^{22}$, $NR^{20}CO_2R^{22}$, $NR^{20}CON(R^{20})_2$, $NR^{20}C(NR^{20})NHR^{23}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OC(O)R^{20}$, $C(O)OCH_2OC(O)R^{20}$, and $OCON(R^{20})_2$ and each optional heteroaryl, aryl, and heterocyclyl substituent is further optionally substituted with halo, $NO_2$, alkyl, $CF_3$, amino, monoalkylamino or dialkylamino, alkylamide, arylamide or heteroarylamide, $NCOR^{22}$, $NR^{20}SO_2R^{22}$, $COR^{20}$, $CO_2R^{20}$, $CON(R^{20})_2$, $NR^{20}CON(R^{20})_2$, $OC(O)R^{20}$, $OC(O)N(R^{20})_2$, $SR^{20}$, $S(O)R^{22}$, $SO_2R^{22}$, $SO_2N(R^{20})_2$, CN, and $OR^{20}$;

$R^{20}$ is selected from the group consisting of H, $C_{1-15}$ alkyl, $C_{2-15}$ alkenyl, $C_{2-5}$ alkynyl, heterocyclyl, aryl, and heteroaryl, which alkyl, alkenyl, alkynyl, heterocyclyl, aryl, and heteroaryl are each optionally substituted with from 1 to 3 substituents independently selected from halo, alkyl, mono- or dialkylamino, alkyl or aryl or heteroaryl amide, CN, $O-C_{1-6}$ alkyl, $CF_3$, aryl, and heteroaryl; and $R^{22}$ is selected from the group consisting of $C_{1-15}$ alkyl, $C_{2-5}$ alkenyl, $C_{2-5}$ alkynyl, heterocyclyl, aryl, and heteroaryl which alkyl, alkenyl, alkynyl, heterocyclyl, aryl, and heteroaryl are each optionally substituted with from 1 to 3 substituents independently selected from halo, alkyl, mono- or dialkylamino, alkyl or aryl or heteroaryl amide, CN, $-O-C_{1-6}$ alkyl, $CF_3$, and heteroaryl.

In a preferred embodiment, X is sulfur, $R^1$ is selected from $-CH_2OH$ or $-CONHEt$; $R^2$ is independently selected from the group consisting of hydrogen, $C_{1-10}$ alkyl and aryl, wherein the alkyl and aryl substituents are optionally substituted with from 1 to 2 substituents independently selected from the group consisting of halo, $OR^{20}$, aryl, $CF_3$, and CN, and wherein each optional aryl substituent is optionally substituted with halo, alkyl, $CF_3$ and CN; $R^3$ and $R^4$ are each individually-selected from the group consisting of hydrogen, $C_{1-15}$ alkyl, aryl, halo, $CF_3$, and CN, wherein the alkyl, and aryl substituents are optionally substituted with a substituent independently selected from the group consisting of halo, $CF_3$, and CN; and $R^{20}$ is selected from H, and $C_{1-6}$.

In a more preferred embodiment, $R^2$ is independently selected from the group consisting of hydrogen, $C_{1-8}$ alkyl and aryl, wherein the alkyl and aryl substituents are optionally substituted with from 1 to 2 substituents independently selected from the group consisting of halo, $OR^{20}$, aryl, $CF_3$, and CN, and wherein each optional aryl substituent is optionally substituted with halo, alkyl, $CF_3$ and CN; $R^3$ and $R^4$ are each individually selected from the group consisting of hydrogen, methyl, and halo; and $R^{20}$ is selected from H, and $C_{1-6}$.

In a still more preferred embodiment, $R^2$ is selected from the group consisting of hydrogen, and $C_{1-8}$ alkyl that is optionally substituted with one aryl substituent that is optionally substituted with halo, alkyl, $CF_3$ and CN; and $R^3$ and $R^4$ are each hydrogen.

In an alternative preferred embodiment, $R^1$ is CONHEt; $R^2$ is selected from the group consisting of hydrogen, and $C_{1-6}$ alkyl that is optionally substituted with aryl that is optionally substituted with alkyl; and $R^3$ and $R^4$ are hydrogen. In the compounds of this invention, the point of attachment to the ring containing the $R^2$, $R^3$ and $R^4$ substituents may be selected from C-3, C-4, or C-5.

It is most preferred that the compound of this invention is selected from the group of compounds consisting of (2R, 3R,4R,5R)-3,4-diacetyloxy-5-[6-chloro-2-(5-methyl(2-thienyl))purin-9-yl]oxolan-2-yl}methyl acetate, (4S,2R,3R, 5R)-2-[6-amino-2-(5-methyl(2-thienyl))purin-9-yl]-5-(hydroxymethyl)oxolane-3,4-diol, 9-{(2R,3R,4R,5R)-3,4-bis(1,1,2,2-tetramethyl-1-silapropoxy)-5-[(1,1,2,2-tetramethyl-1-silapropoxy)methyl]oxolan-2-yl}-2-(5-iodo(2-thienyl))purine-6-ylamine, (4S,2R,3R,5R)-2-[6-amino-2-(5-iodo(2-thinyl)purin-9-yl]-5-(hydroxymethyl)oxolane-3, 4-diol, 9-{(2R,3R,4R, 5R)-3,4-bis(1,1,2,2-tetramethyl-1-silapropoxy)-5-[(1,1,2,2-tetramethyl-1-silapropoxy)methyl]oxolan-2-yl}-2-(5-phenyl(2-thienyl))purine-6-ylamine; 4S,2R,3R,5R)-2-[6-amino-2-(5-phenyl(2-thienyl))purin-9-yl]-5-(hydroxymethyl)oxolane-3,4-diol, and mixtures thereof.

The following definitions apply to terms as used herein.

"Halo" or "Halogen" —alone or in combination means all halogens, that is, chloro (C1), fluoro (F), bromo (Br), iodo (I).

"Hydroxyl" refers to the group —OH.

"Thiol" or "mercapto" refers to the group —SH.

"Alkyl" —alone or in combination means an alkane-derived radical containing from 1 to 20, preferably 1 to 15, carbon atoms (unless specifically defined). It is a straight chain alkyl, branched alkyl or cycloalkyl. Preferably, straight or branched alkyl groups containing from 1–15, more preferably 1 to 8, even more preferably 1–6, yet more preferably 1–4 and most preferably 1–2, carbon atoms, such as methyl, ethyl, propyl, isopropyl, butyl, t-butyl and the like. The term "lower alkyl" is used herein to describe the straight chain alkyl groups described immediately above. Preferably, cycloalkyl groups are monocyclic, bicyclic or tricyclic ring systems of 3–8, more preferably 3–6, ring members per ring, such as cyclopropyl, cyclopentyl, cyclohexyl, adamantyl and the like. Alkyl also includes a straight chain or branched alkyl group that contains or is interrupted by a cycloalkyl portion. The straight chain or branched alkyl group is attached at any available point to produce a stable compound. Examples of this include, but are not limited to, 4-(isopropyl)-cyclohexylethyl or 2-methyl-cyclopropylpentyl. A substituted alkyl is a straight chain alkyl, branched alkyl, or cycloalkyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Alkenyl" —alone or in combination means a straight, branched, or cyclic hydrocarbon containing 2–20, preferably 2–17, more preferably 2–10, even more preferably 2–8, most preferably 2–4, carbon atoms and at least one, preferably 1–3, more preferably 1–2, most preferably one, carbon to carbon double bond. In the case of a cycloalkyl group, conjugation of more than one carbon to carbon double bond is not such as to confer aromaticity to the ring. Carbon to carbon double bonds may be either contained within a cycloalkyl portion, with the exception of cyclopropyl, or within a straight chain or branched portion. Examples of alkenyl groups include ethenyl, propenyl, isopropenyl, butenyl, cyclohexenyl, cyclohexenylalkyl and the like. A substituted alkenyl is the straight chain alkenyl, branched alkenyl or cycloalkenyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, carboxy, alkoxycarbonyl, aryloxycarbonyl, heteroaryloxycarbonyl, or the like attached at any available point to produce a stable compound. "Alkynyl" —alone or in combination means a straight or branched hydrocarbon containing 2–20, preferably 2–17, more preferably 2–10, even more preferably 2–8, most preferably 2–4, carbon atoms containing at least one, preferably one, carbon to carbon triple bond. Examples of alkynyl groups include ethynyl, propynyl, butynyl and the like. A substituted alkynyl refers to the straight chain alkynyl or branched alkenyl defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like attached at any available point to produce a stable compound.

"Alkyl alkenyl" refers to a group —R—CR'=CR''' R'''', where R is lower alkyl, or substituted lower alkyl, R', R''', R'''' may independently be hydrogen, halogen, lower alkyl, substituted lower alkyl, acyl, aryl, substituted aryl, hetaryl, or substituted hetaryl as defined below.

"Alkyl alkynyl" refers to a groups —RC≡—CR' where R is lower alkyl or substituted lower alkyl, R' is hydrogen, lower alkyl, substituted lower alkyl, acyl, aryl, substituted aryl, hetaryl, or substituted hetaryl as defined below.

"Alkoxy" denotes the group —OR, where R is lower alkyl, substituted lower alkyl, acyl, aryl, substituted aryl, aralkyl, substituted aralkyl, heteroalkyl, heteroarylalkyl, cycloalkyl, substituted cycloalkyl, cycloheteroalkyl, or substituted cycloheteroalkyl as defined.

"Alkylthio" denotes the group —SR, –S(O)$_{n=1}$—R, where R is lower alkyl, substituted lower alkyl, aryl, substituted aryl, aralkyl or substituted aralkyl as defined herein.

"Acyl" denotes groups —C(O)R, where R is hydrogen, lower alkyl substituted lower alkyl, aryl, substituted aryl and the like as defined herein.

"Aryloxy" denotes groups —OAr, where Ar is an aryl, substituted aryl, heteroaryl, or substituted heteroaryl group as defined herein.

"Amino" denotes the group NRR', where R and R' may independently by hydrogen, lower alkyl, substituted lower alkyl, aryl, substituted aryl, hetaryl, or substituted hetaryl as defined herein or acyl.

"Amido" denotes the group —C(O)NRR', where R and R' may independently by hydrogen, lower alkyl, substituted lower alkyl, aryl, substituted aryl, hetaryl, substituted hetaryl as defined herein.

"Carboxyl" denotes the group —C(O)OR, where R is hydrogen, lower alkyl, substituted lower alkyl, aryl, substituted aryl, hetaryl, and substituted hetaryl as defined herein.

"Aryl" —alone or in combination means phenyl or naphthyl optionally carbocyclic fused with a cycloalkyl of preferably 5–7, more preferably 5–6, ring members and/or optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Substituted aryl" refers to aryl optionally substituted with one or more functional groups, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heterocycle" refers to a saturated, unsaturated, or aromatic carbocyclic group having a single ring (e.g., morpholino, pyridyl or furyl) or multiple condensed rings (e.g., naphthpyridyl, quinoxalyl, quinolinyl, indolizinyl or benzo[b]thienyl) and having at least one hetero atom, such as N, O or S, within the ring, which can optionally be unsubstituted or substituted with, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heteroaryl" —alone or in combination means a monocyclic aromatic ring structure containing 5 or 6 ring atoms, or a bicyclic aromatic group having 8 to 10 atoms, containing one or more, preferably 1–4, more preferably 1–3, even more preferably 1–2, heteroatoms independently selected from the group O, S, and N, and optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable aromatic ring is retained. Examples of heteroaryl groups are pyridinyl, pyridazinyl, pyrazinyl, quinazolinyl, purinyl, indolyl, quinolinyl, pyrimidinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, indolyl and the like. A substituted heteroaryl contains a substituent attached at an available carbon or nitrogen to produce a stable compound.

"Heterocyclyl"—alone or in combination means a non-aromatic cycloalkyl group having from 5 to 10 atoms in which from 1 to 3 carbon atoms in the ring are replaced by heteroatoms of O, S or N, and are optionally benzo fused or fused heteroaryl of 5–6 ring members and/or are optionally substituted as in the case of cycloalkyl. Heterocycyl is also intended to include oxidized S or N, such as sulfinyl, sulfonyl and N-oxide of a tertiary ring nitrogen. The point of attachment is at a carbon or nitrogen atom. Examples of heterocyclyl groups are tetrahydrofuranyl, dihydropyridinyl, piperidinyl, pyrrolidinyl, piperazinyl, dihydrobenzofuryl, dihydroindolyl, and the like. A substituted hetercyclyl contains a substituent nitrogen attached at an available carbon or nitrogen to produce a stable compound.

"Substituted heteroaryl" refers to a heterocycle optionally mono or poly substituted with one or more functional groups, e.g., halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Aralkyl" refers to the group —R—Ar where Ar is an aryl group and R is lower alkyl or substituted lower alkyl group. Aryl groups can optionally be unsubstituted or substituted with, e.g., halogen, lower alkyl, alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Heteroalkyl" refers to the group —R—Het where Het is a heterocycle group and R is a lower alkyl group. Heteroalkyl groups can optionally be unsubstituted or substituted with e.g., halogen, lower alkyl, lower alkoxy, alkylthio, acetylene, amino, amido, carboxyl, aryl, aryloxy, heterocycle, substituted heterocycle, hetaryl, substituted hetaryl, nitro, cyano, thiol, sulfamido and the like.

"Heteroarylalkyl" refers to the group —R—HetAr where HetAr is an heteroaryl group and R lower alkyl or substituted lower alkyl. Heteroarylalkyl groups can optionally be unsubstituted or substituted with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like.

"Cycloalkyl" refers to a divalent cyclic or polycyclic alkyl group containing 3 to 15 carbon atoms.

"Substituted cycloalkyl" refers to a cycloalkyl group comprising one or more substituents with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like.

"Cycloheteroalkyl" refers to a cycloalkyl group wherein one or more of the ring carbon atoms is replaced with a heteroatom (e.g., N, O, S or P).

Substituted cycloheteroalkyl" refers to a cycloheteroalkyl group as herein defined which contains one or more substituents, such as halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Alkyl cycloalkyl" denotes the group —R-cycloalkyl where cycloalkyl is a cycloalkyl group and R is a lower alkyl or substituted lower alkyl. Cycloalkyl groups can optionally be unsubstituted or substituted with e.g. halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Alkyl cycloheteroalkyl" denotes the group —R-cycloheteroalkyl where R is a lower alkyl or substituted lower alkyl. Cycloheteroalkyl groups can optionally be unsubstituted or substituted with e.g. halogen, lower alkyl, lower alkoxy, alkylthio, amino, amido, carboxyl, acetylene, hydroxyl, aryl, aryloxy, heterocycle, substituted heterocycle, hetaryl, substituted hetaryl, nitro, cyano, thiol, sulfamido and the like.

Compounds of this invention can be prepared according to the methods outlined in the schemes 1–2. 2-Stannyladenosine 1 was prepared in three steps from commercially available 6-chloropurine riboside following literature procedure (K. Kato et.al., *J. Org. Chem.* (1997), 62, 6833–6841). Tri TBDMS derivative 3 was obtained by treating 2 with TBDMSCI and imidazole in DM. Lithiation with LTMP followed by quenching with tri n-butyltin chloride gave exclusively 2-stannyl derivative 4. Ammonolysis in 2-propanol gave 2-stannyladenosine 1. Stille coupling of 1 with commercially available 2,5-diiodothiophene in presence of Pd(PPh$_3$)$_4$ and CuI resulted in 5 (K. Kato et.al., *J. Org. Chem.* (1997), 62, 6833–6841). Deprotection of silyl groups on 2',3' and 5' hydroxyls with 0.5 M ammonium fluoride in methanol gave 6 (Scheme 1).

Scheme 1

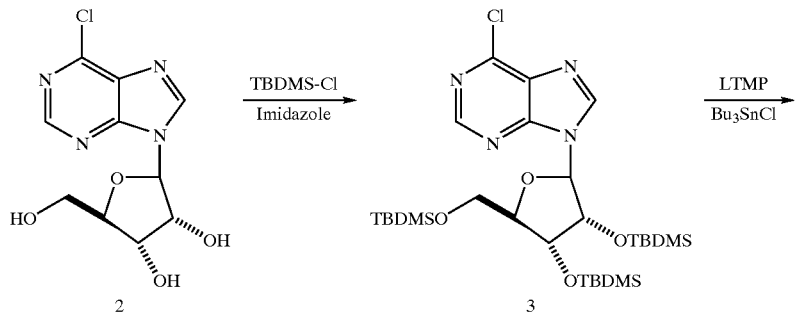

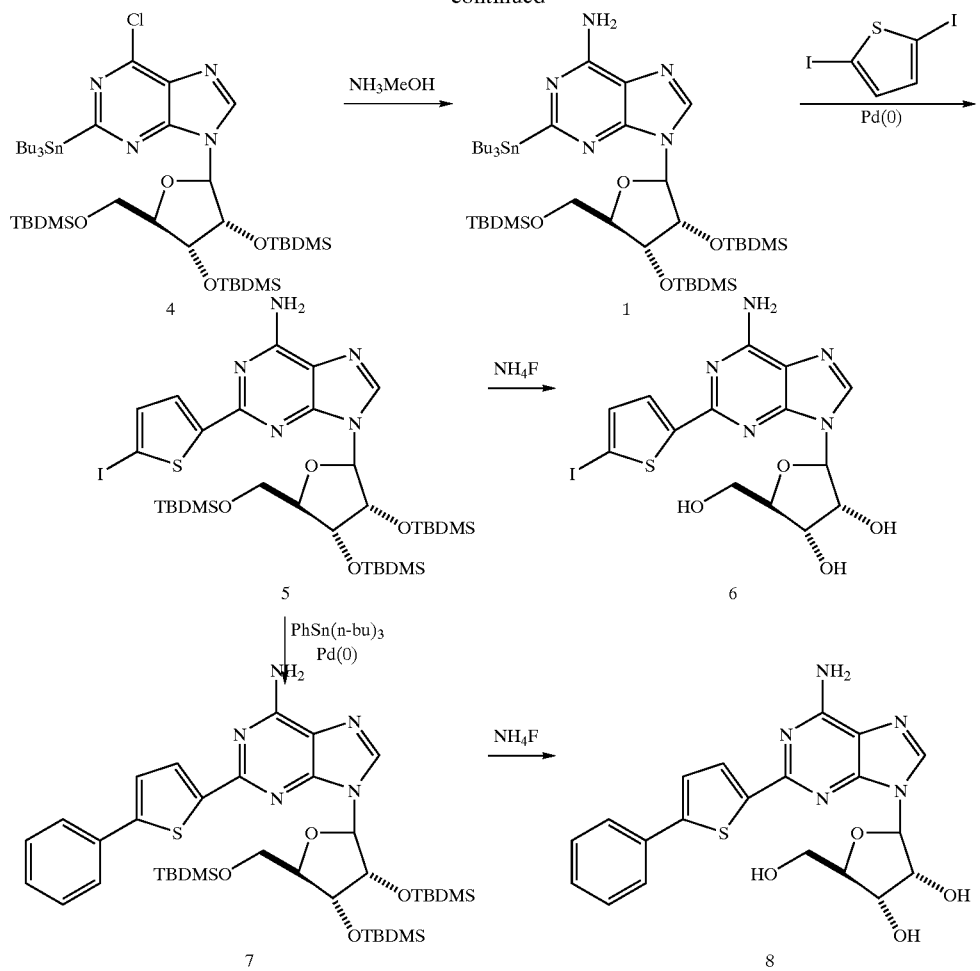
Phenylthiophene derivative 8 was prepared by treating iodothiophene derivative 5 with commercially available tri-n-butylphenyltin to give compound 7 which was deprotected with 0.5 M NH4F.
Scheme 2
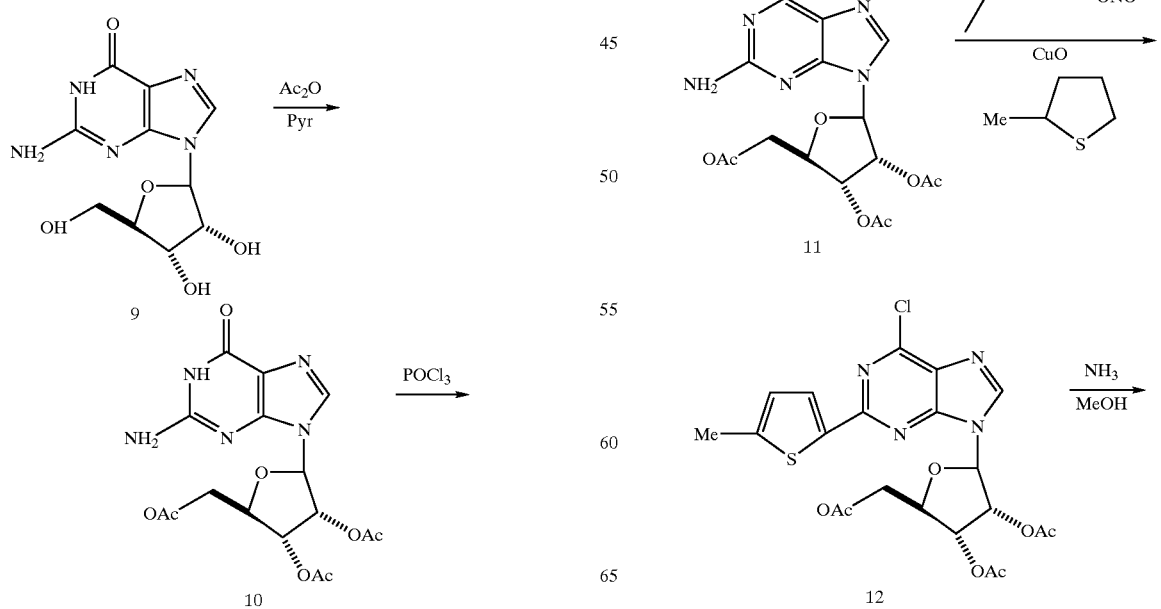

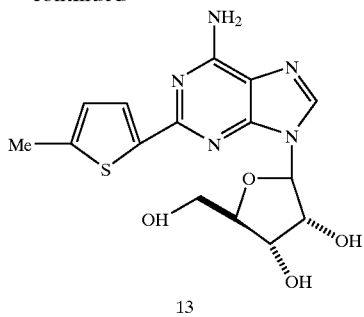

13

A specific synthesis of compound 13 is illustrated in Scheme 2. Commercially available guanosine 9 was converted to the triacetate 10 as previously described (M. J. Robins and B. Uznanski, *Can. J Chem.* (1981), 59, 2601–2607). Compound 11, prepared by following the literature procedure of Cerster et al. (J. F. Cerster, A. F. Lewis, and R. K. Robins, *Org. Synthesis*, 242–243), was converted to compounds 13 in two steps as previously described for similar type of compounds (Matsuda et al., Synthesis, (1984), 963.

Compounds of this invention are useful in conjunction with radioactive imaging agents to image coronary activity. The compounds of this invention are $A_{2A}$ agonists that are believed to provide specific activation of adenosine $A_{2A}$ receptors in the coronary vessels as opposed to adenosine $A_1$ receptors in the atrium and AV-node and/or $A_{2B}$ receptors in peripheral vessels, thus avoiding undesirable side-effects. Upon administration in a therapeutic amount, the compounds of this invention cause coronary blood vessels to vasodilate to induce coronary steal wherein healthy coronary vessels steal blood from unhealthy vessels resulting in lack of blood flow to heart tissues. Coronary imaging then identified coronary regions with healthy and unhealthy blood flow. Lower doses of the $A_{2A}$ agonists may provide beneficial coronary vasodilatation (less severe) in the treatment of chronic CAD.

As $A_{2A}$ agonists, the compounds of this invention are also useful in adjunctive therapy with angioplasty to induce dilation, inhibit platelet aggregation, and as a general anti-inflammatory agent. $A_{2A}$ agonists, such as the compounds of this invention, can provide the therapeutic benefits described above by preventing neutrophil activation (Purinergic Approaches in Experimental Therapeutics K. A. Jacobson and M. F. Jarvis 1997 Wiley, New York). The compounds of this invention are also effective against a condition called no-reflow in which platelets and neutrophils aggregate and block a vessel. As $A_{2A}$ agonists, the compounds of this invention are effective against no-reflow by preventing neutrophil and platelet activation (e.g., they are believed to prevent release of superoxide from neutrophils). As $A_{2A}$ agonists, the compounds of this invention are also useful as cardioprotective agents through their anti-inflammatory action on neutrophils. Thus, in situations when the heart will go through an ischemic state such as a transplant, they will be useful.

This invention also includes pro-drugs of the above-identified $A_{2A}$ agonists. A pro-drug is a drug which has been chemically modified and may be biological inactive at its site of action, but which will be degraded or modified by one or more enzymatic or in vivo processes to the bioactive form. The pro-drugs of this invention should have a different pharnacokinetic profile to the parent enabling improved absorption across the mucosal epithelium, better salt formulation and/or solubility and improved systemic stability. The above-identified compounds may be preferably modified at one or more of the hydroxyl groups. The modifications may be (1) ester or carbanate derivatives which may be cleaved by esterases or lipases, for example; (2) peptides which may be recognized by specific or non-specific proteinase; or (3) derivatives that accumulate at a site of action through membrane selection or a pro-drug form or modified pro-drug form, or any combination of (1) to (3) above.

It It The compositions may be administered orally, intravenously, through the epidermis or by any other means known in the art for administering a therapeutic agents. The method of treatment comprises the administration of an effective quantity of the chosen compound, preferably dispersed in a pharmaceutical carrier. Dosage units of the active ingredient are generally selected from the range of 0.01 to 100 mg/kg, but will be readily determined by one skilled in the art depending upon the route of administration, age and condition of the patient. This dose is typically administered in a solution about 5 minutes to about an hour or more prior to coronary imaging. No unacceptable toxicological effects are expected when compounds of the invention are administered in therapeutic amounts.

If the final compound of this invention contains a basic group, an acid addition salt may be prepared. Acid addition salts of the compounds are prepared in a standard manner in a suitable solvent from the parent compound and an excess of acid, such as hydrochloric, hydrobromic, sulfuric, phosphoric, acetic, maleic, succinic, or methanesulfonic. The hydrochloric salt form is especially useful. If the final compound contains an acidic group, cationic salts may be prepared. Typically the parent compound is treated with an excess of an alkaline reagent, such as hydroxide, carbonate or alkoxide, containing the appropriate cation. Cations such as $Na^+$, $K^+$, $Ca^{+2}$ and $NH_4^+$ are examples of cations present in pharmaceutically acceptable salts. Certain of the compounds form inner salts or zwitterions which may also be acceptable.

Pharmaceutical compositions including the compounds of this invention, and/or derivatives thereof, may be formulated as solutions or lyophilized powders for parenteral administration. Powders may be reconstituted by addition of a suitable diluent or other pharmaceutically acceptable carrier prior to use. If used in liquid form the compounds of this invention are preferably incorporated into a buffered, isotonic, aqueous solution. Examples of suitable diluents are normal isotonic saline solution, standard 5% dextrose in water and buffered sodium or ammonium acetate solution. Such liquid formulations are suitable for parenteral administration, but may also be used for oral administration. It may be desirable to add excipients such as polyvinylpyrrolidinone, gelatin, hydroxycellulose, acacia, polyethylene glycol, mannitol, sodium chloride, sodium citrate or any other excipient known to one of skill in the art to pharmaceutical compositions including compounds of this invention. Alternatively, the pharmaceutical compounds may be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, teffa alba, magnesium stearate or stearic acid, talc, pectin, acacia, agar or gelatin. The carrier may also include a sustained release material such as glycerol monostearate or glycerol distearate, alone or with a wax. The amount of solid carrier varies but, preferably, will be between about 20 mg to about 1 gram per dosage unit. The pharmaceutical dosages are made using conventional techniques such as milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly or filled into a soft gelatin capsule. It is preferred that the compositions of this invention are administered as a solution either orally or intravenously. The Examples which follow serve to illustrate this invention. The Examples are intended to in no way limit the scope of this invention, but are provided to show how to make and use the compounds of this invention. In the Examples, all temperatures are in degrees Centigrade.

EXAMPLE 1

{(2R,3R,4R,5R)-3,4-Diacetyloxy-5-[6-chloro-2-(5-methyl(2-thienyl))purin-9-yl]oxolan-2-yl}methyl Acetate (12)

To a suspension of 2-Amino-6-chloro-9-(2', 3', 5'-tri-O-acetyl)-D-ribofuranosylpurine (11) (170.0 mg, 0.4 mmol) in 2 mL 2-methylthiophene, was added isoamyl nitrite (250 mL), CuI (60 mg) and the mixture was heated at 115° C. for 3 h. The reaction mixture was filtered, concentrated under vacuo and the residue was purified using prep. TLC (EtOAc:Hexanes 1:1) to afford 12. $^1$HNMR (CDCl$_3$)δ2.0 (s, 3 H), 2.05 (s, 3 H), 2.1 (s, 3 H), 2.5 (s, 3 H), 4.30 (m, 1 H), 4.40–4.55 (m, 2 H), 5.90 (t, 1 H), 6.1 (d, 1 H), 6.8 (d, 1 H), 7.85 (d, 1 H), 8.1 (s, 1 H).

EXAMPLE 2

(4S,2R,3R,5R)-2-[6-Amino-2-(5-methyl(2-thienyl))purin-9-yl]-5-(hydroxymethyl)oxolane-3,4-diol (13).

Compound 12 (50 mg, 0.1 mmol) was dissolved in 5 mL methanolic ammonia (saturated at 0° C.) and the mixture was heated at 40° C. for 24 h. After concentration in vacuo, the residue was purified using prep. TLC (10% MeOHlDCM) to afford 13 $^1$HNMR (CD3OD)δ2.5 (s, 3 H) 3.75 (d, 1 H), 3.85 (d, 1 H), 4.15 (d, 2 H) 4.45 (m, 1 H), 4.85 (m, 1 H), 6.0 (d, 1 H), 6.75 (d, 1 H), 7.7 (d, 1 H), 8.25 (s, 1 H).

EXAMPLE 3

Compounds of this invention were assayed to determine their affinity for the $A_{2A}$ receptor in a pig striatum membrane prep. Briefly, 0.2 mg of pig striatal membranes were treated with adenosine deaminase (2 U/mL) and 50 mM Tris buffer (pH=7,4) followed by mixing. To the pig membranes was added 2 mL of serially diluted DMSO stock solution of the compounds of this invention at concentrations ranging from 10 nM to 100 μM or the control received 2 mL of DMSO alone, then the: antagonist ZM 241385 in Tris buffer (50 mM, pH of 7.4) was added to achieve a final concentration of 2 nM. After incubation at 23° C. for 2h, then the solutions were filtered using a membrane harvester using multiple washing of the membranes (3x). The filter disks were counted in scintillation cocktail to determine the amount of displacement of tritiated ZM displaced by the compounds of this invention. Greater than a 5 point curve was used to generate Ki's. Compound 13 has a Ki between 1,000 and 10,000 nM.

EXAMPLE 4

Additional compounds of this invention were prepared as follows:

9-{(2R,3R,4R,5R)-3,4-bis(1,1,2,2-tetramethyl-1-silapropoxy)-5-[(1,1,2,2-tetramethyl-1-silapropoxy)methyl]oxolan-2-yl}-2-(5-iodo(2-thienyl))purine6-ylamine (5).

A mixture of compound 4 (50 mg, 0.056 mmol), 2,5-diiodopyrazole (50 mg), Pd(PPh3)4 (20 mg, 15 mol %) and CuI (40 mg, 0.2 mmol) in DMF (1 mL) was stirred at 90 C for 16 h. The reaction was concentrated in vacuo and the residue was purified by preparative thin layer chromatography (methylene chloride: methanol 10:1) to afford compound 5: 1H NMR(CDCl3) 0.00(s, 3H, CH3), 0.01(s, 3H, CH3), 0.04(s, 3H, CH3), 0.07 (s, 3H, CH3), 0.11 (s, 3H, CH3), 0.14 (s, 3H, CH3), 0.78 (s, 9H, t-bu), 0.83 (s, 9H, t-bu), 0.91 (s, 9H, t-bu), 3.80 (d, 1H), 4.05 (d, 1H), 4.11–4.12 (m, 1H), 4.32–4.33 (m, 1H), 4.80 (d, 1H), 5.55 (bs, 2H, D2O exchangeable), 5.95 (d, 1H), 7.21 (d, 2H), 7.50 (d, 2H), 8.10 (s, 1H).

(4S,2R,3R,5R)-2-[6-Amino-2-(5-iodo(2-thienyl))purin-9-yl]-5-(hydroxymethyl)oxolane-3,4-diol(6).

A solution of triTBDMS derivative (5) (15 mg) in 0.5 M solution of NH4F in methanol (5mL) was refluxed for 16 h. The reaction mixture was concentrated and the residue was purified by preparative TLC (methanol-dichloromethane 9:1) to afford 6; 1H NMR (CD3OD) 3.65 (d, J=11.2 Hz, 1H), 3.81 (d, J=11.2 Hz, 1H), 4.15–4.16 (m, 1H), 4.25–4.26 (m,1H), 4.78 (dd, 1H), 5.72 (d, 1H), 7.15 (s, 2H), 7.45 (d, 2H), 7.80 (s, 1H).

9-{(2R,3R,4R,5R)-3,4-bis(1,1,2,2-tetramethyl-1-silapropoxy)-5-[(1,1,2,2-tetramethyl-1-silapropoxy)methyl]oxolan-2-yl}-2-(5-phenyl(2-thienyl))purine-6-ylamine(7).

A mixture of compound 5 (20 mg, 0.056 mmol), tri n-butylphenyltin (50 mg), Pd(PPh3)4 (20 mg, 15 mol %) and CuI (40 mg, 0.2 mmol) in DMF (1mL) was stirred at 90 C for 16 h. The reaction was concentrated in vacuo and the residue was purified by preparative thin layer chromatography (methylene chloride: methanol 10:1) to afford compound 7: 1H NMR(CDCl3) 0.00(s, 3H, CH3), 0.01(s, 3H, CH3), 0.04(s, 3H, CH3), 0.07 (s, 3H, CH3), 0.11 (s, 3H, CH3), 0.14 (s, 3H, CH3), 0.78 (s, 9H, t-bu), 0.83 (s, 9H, t-bu), 0.91 (s, 9H, t-bu), 3.80 (d, 1H), 4.05 (d, 1H), 4.11–4.12 (m, 1H), 4.32–4.33 (m, 1H), 4.80 (d, 1H), 5.55 (bs, 2H, D2O exchangeable), 5.95 (d, 1H), 7.25–7.4 (m, 5H), 7.65 (d, 2H), 7.85 (d,1H), 8.12 (s, 1H).

(4S,2R,3R,5R)-2-[6-amino-2-(5-phenyl(2-thienyl))purin-9-yl]-5-(hydroxymethyl)oxolane-3,4diol(8).

A solution of triTBDMS derivative 7 (5 mg) in 0.5 M solution of NH4F in methanol (5 mL) was refluxed for 16 h. Reaction mixture was concentrated and residue was purified by preparative TLC (methanol-dichloromethane 9:1) to afford 8; 1H NMR (CD3OD) 3.65 (d, J=11.2 Hz, 1H), 3.81 (d, J=11.2 Hz, 1H), 4.15–4.16 (m, 1H), 4.22–4.26 (m,1H), 4.74 (dd, 1H), 5.74 (d, 1H), 7.10–7.25 (m, 5H), 7.45 (d, 2H), 7.74 (d, 2H), 7.87 (s, 1H).

What we claim is:

1. A compound having the following formula:

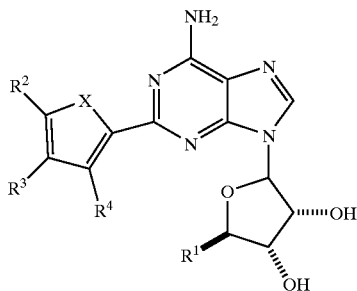

wherein $R^1$ is —CH$_2$OH or —CONHEt;

X is S;

$R^2$ is selected from the group consisting of hydrogen, $C_{1-8}$ alkyl, aryl, and halo wherein the alkyl and aryl substituents are optionally substituted with from 1 to 2 substituents independently selected from the group consisting of halo, OR$^{20}$, aryl, CF$_3$, and CN, and wherein each optional aryl substituent is optionally substituted with a substituent selected from the group consisting of halo, alkyl, CF$_3$ and CN;

$R^3$ and $R^4$ are each individually selected from the group consisting of hydrogen, methyl, and halo; and $R^{20}$ is selected from hydrogen or $C_{1-6}$ alkyl wherein, when $R^1$ is —CH$_2$OH, then $R^2$ cannot be hydrogen.

2. The compound of claim 1 wherein $R^1$ is —CH$_2$OH;

$R^2$ is selected from the group consisting of $C_{1-8}$ alkyl and aryl, wherein the alkyl and aryl substituents are optionally substituted with 1 substituent selected from the group consisting of halo, aryl, CF$_3$, and CN, and wherein each optional aryl substituent is optionally substituted with a substituent selected from the group consisting of halo, alkyl, CF$_3$ and CN; and $R^3$ and $R^4$ are each individually selected from the group consisting of hydrogen and methyl.

3. The compound of claim 1 wherein $R^1$ is —CH$_2$OH, $R^2$ is selected from the group consisting of $C_{1-8}$ alkyl that is optionally substituted with 1 substituent selected from the group consisting of aryl, CF$_3$, and CN, and wherein each optional aryl substituent is optionally substituted with a substituent selected from the group consisting of halo, alkyl, CF$_3$ and CN; and $R^3$ and $R^4$ are each individually selected from the group consisting of hydrogen and methyl.

4. The compound of claim 1 wherein $R^1$ is —CH$_2$OH;

$R^2$ is $C_{1-8}$ alkyl that is optionally substituted with one aryl substituent that is optionally substituted with a substituent selected from the group consisting of halo, alkyl, CF$_3$ and CN; and $R^3$ and $R^4$ are each hydrogen.

5. The compound of claim 1 wherein $R^1$ is —CH$_2$OH;

$R^2$ is $C_{1-6}$ alkyl that is optionally substituted with aryl that is optionally substituted with alkyl; and $R^3$ and $R^4$ are each hydrogen.

6. The compound of claim 1 wherein $R^1$ is —CONHEt;

$R^2$ is selected from the group consisting of hydrogen and $C_{1-8}$ alkyl that is optionally substituted with 1 substituent selected from the group consisting of aryl, CF$_3$, and CN, and wherein each optional aryl substituent is optionally substituted with a substituent selected from the group consisting of halo, alkyl, CF$_3$ and CN; and $R^3$ and $R^4$ are each individually selected from the group consisting of hydrogen and methyl.

7. The compound of claim 1 wherein $R^1$ is —CONHEt;

$R^2$ is selected from the group consisting of hydrogen and $C_{1-8}$ alkyl that is optionally substituted with 1 aryl substituent that is optionally substituted with a substituent selected from the group consisting of halo, alkyl, CF$_3$ and CN; and $R^3$ and $R^4$ are each hydrogen.

8. The compound of claim 1 wherein $R^1$ is —CONHEt;

$R^2$ is selected from the group consisting of hydrogen and $C_{1-6}$ alkyl that is optionally substituted with aryl that is optionally substituted with alkyl; and $R^3$ and $R^4$ are hydrogen.

9. The compound of claim 1 wherein $R^1$ is —CH$_2$OH;

X is S;

$R^2$ is selected from the group consisting of halo, $C_{1-6}$ alkyl that is substituted with halo or with aryl, aryl that is that is optionally substituted with $C_{1-6}$ alkyl, aryl or halo; and $R^3$ and $R^4$ are each hydrogen.

10. A compound selected from the group consisting of 2-(2-(5-methylthienyl))adenosine; 2-(2-(5-iodothienyl)) adenosine; and 2-(2-(5-phenylthienyl))adenosine.

11. A pharmaceutical composition of comprising a compound of claim 1 and one or more pharmaceutically acceptable excipients.

12. The pharmaceutical composition of claim 11 wherein the pharmaceutical composition is in the form of a solution.

13. A method for stimulating coronary vasodilation in a mammal by administering to the mammal a therapeutically effective amount of a compound of claim 1 that is sufficient to stress the heart and induce a coronary steal situation for the purposes of imaging the heart.

14. The method of claim 13 wherein the therapeutically effective amount ranges from about 0.01 to about 100 mg/kg weight of the mammal.

15. The method of claim 14 wherein the mammal is a human.

16. A method for treating humans comprising administering a therapeutic amount of the pharmaceutical composition of claim 1 to a human in order to treat a condition selected from the group consisting of providing adjunctive therapy with angioplasty, to induce dilation, to inhibit platelet aggregation, to treat inflammation and to treat no-reflow.

* * * * *